United States Patent [19]

Yabe

[11] 4,204,259
[45] May 20, 1980

[54] AUTOMATIC APPARATUS FOR CONTINUOUS DETERMINATION OF BORON AND LITHIUM CONCENTRATIONS

[75] Inventor: Ikuo Yabe, Tokyo, Japan

[73] Assignee: Nikkiso Co., Ltd., Tokyo, Japan

[21] Appl. No.: 895,367

[22] Filed: Apr. 11, 1978

[51] Int. Cl.² .................. G06F 15/52; G01N 27/42
[52] U.S. Cl. .................. 438/497; 176/19 EC; 324/438; 364/504
[58] Field of Search .................. 364/497, 499, 504; 324/29, 30 R, 30 B; 176/19 R, 19 EC, 50, 51

[56] References Cited

U.S. PATENT DOCUMENTS

| | | | |
|---|---|---|---|
| 3,941,665 | 3/1976 | Eckfeldt et al. | 324/30 R |
| 4,028,618 | 6/1977 | Teass, Jr. | 324/30 R |
| 4,035,719 | 7/1977 | Anderson | 324/30 R |

*Primary Examiner*—Jerry Smith

[57] ABSTRACT

There is disclosed an apparatus including a calculating circuit for automatic determination of the boron concentration with the Li-ion concentration of the primary cooling water in a pressurized water atomic power plant. The conductivity of a sample of the cooling water is measured before and after the sample water is mixed with a mannitol solution; the Li-ion concentration is calculated from the measurement obtained and the correct boron concentration is calculated with correction based on the Li-ion concentration.

6 Claims, 5 Drawing Figures

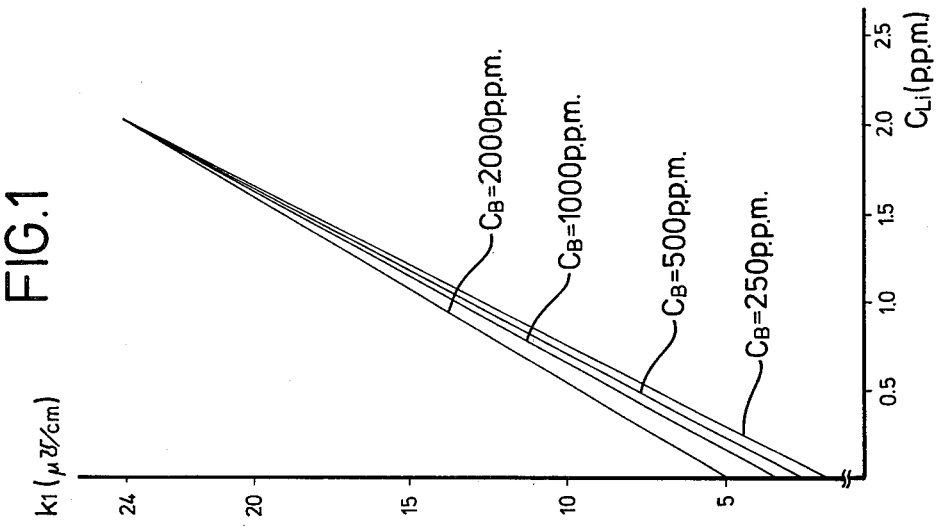
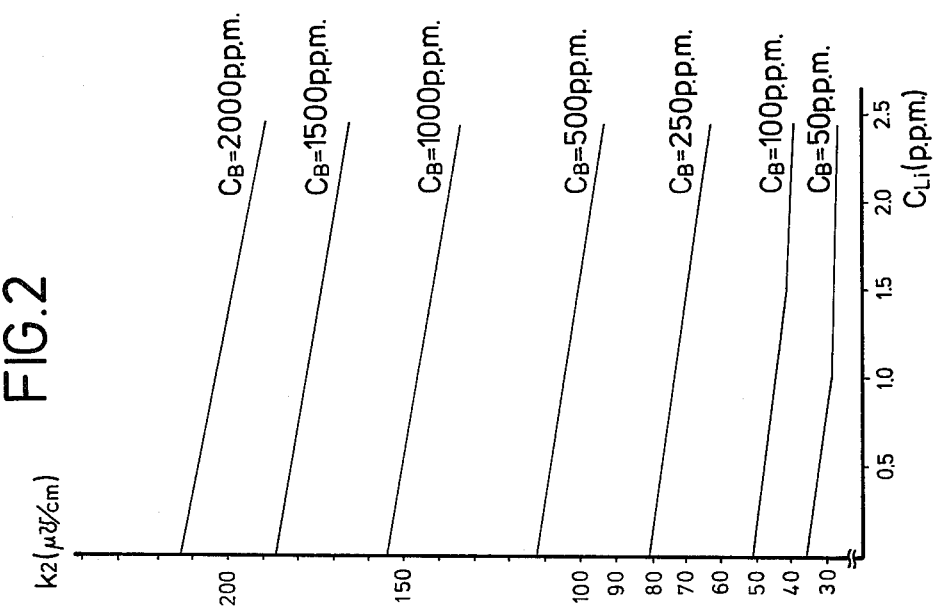

AUTOMATIC APPARATUS FOR CONTINUOUS DETERMINATION OF BORON AND LITHIUM CONCENTRATIONS

BACKGROUND OF THE INVENTION

This invention relates to an automatic apparatus for determination of the boron and Li-ion concentrations of the primary cooling water in a pressurized water reactor plant.

Generally, the output of the pressurized water reactor is controlled by adding the boron to the primary cooling water and by changing the concentration thereof. Therefore, the determination of the boron concentration is essential for the operation control of the reactor.

Since the boric acid sample water is a weak acid similar to a non-electrolyte, it has hitherto been proposed that a mannitol or other polyvalent alcohol solution be added with a certain mixing ratio to the boric acid sample water to form a boric acid-mannitol complex, thereby to increase the conductivity for the measurement thereof with an electrode so that the boron concentration (p.p.m.) may be calculated from the mutual relation between the conductivity and the boron concentration.

However, the primary cooling water of a pressurized water reactor contains not only boron of the order of 1,000 ppm but also other cations such as Li-ion of the order of 1 ppm which lead to the erroneous measurement of the conductivity, because LiOH especially is a strong electrolyte.

Therefore, the sample water has hitherto been passed through an ion exchange resin to first remove cations (especially Li-ion), and then the mannitol solution is added for measurement of the conductivity to avoid a detrimental influence of the cation contained in the sample water.

After the ion exchange resin material has been used for the measurement, the deteriorated or contaminated resin must be quickly replaced by fresh resin material. However, on the treatment of the primary cooling water in the atomic power plant, the radioactive matter such as Li is precipitated in or absorbed by the resin material with elevated level of the radioactivity. If the operator directly touches the radioactively contaminated resin, he will likely become exposed to dangerous radioactivity and hence the handling of the waste resin becomes extremely difficult.

In view of the foregoing, a convenient and safe system has now been found for replacing the waste or contaminated ion exchange resin from a fixed container for precipitating or absorbing the radioactive material contained in the sample. The container, at its inlet side, is connected to a flexible tube communicating with a boric acid sample water supply system through a quick connector. The fixed container at its outlet side is connected through a three way valve to a boron concentration measuring system and to a water supply and drain system in which one or more exchangeable containers for storing fresh resin and/or receiving the waste material transferred from the fixed container is releasably arranged in juxtaposition with the fixed container. Said exchangeable container at its opposite ends is provided with quick connecting terminals, one of which is releasably connected to a mating quick connector terminal secured to the end of the flexible tube, whereas the other terminal is connected to a mating quick connector terminal of the tube connected to the three way valve, which selectively communicates with the water supply or drain system.

The fixed container containing the deteriorated or waste resin is connected at its inlet side to one end of the flexible tube which, at its opposite end, is in turn connected to the exchangeable container for recovering the waste resin so that the waste resin is transferred from the fixed container to the exchangeable container under water pressure by the operation of the three way valve. Then, the exchangeable container for recovering the waste resin is replaced by another exchangeable container containing therein fresh active resin which is subsequently transferred into the field container with water supplied by the operation of the three way valve. Finally, the flexible tube connected to the inlet side of the fixed container is returned to its original position to achieve a convenient and quick replacement of the waste or contaminated resin by the fresh and active resin.

In this system, two separate exchangeable containers are arranged in connected relation to the fixed container. The first exchangeable container is filled with fresh resin material and a second container is left empty. In this arrangement, the contaminated ion exchange resin material in the fixed container is transferred into the second or vacant container and the fresh resin contained in the first container is then moved into the fixed container. When the resin material in the fixed container is contaminated, it is fed back to the first container. Thereafter, the first and second exchangeable containers, each containing contaminated resin materials, are replaced by another first container filled with resin material and a second container left empty for the next replacement operation.

The exchangeable containers may be made of a transparent material such as transparent synthetic resin with a desired scale indication provided on the surface of the container for indicating the quantity of the resin to be received, so that the replacement of the proper amount of resin may be conveniently observed.

As described hereinbefore, the determination of the boron concentration may be carried out without errors by use of the ion exchange resin. In employing an ion exchange resin, however, the determination result is obtained following a time lag during which the adsorption of Li-ion increases, resulting in the accumulation of the radioactive substance in the resin material. As the result, the radioactivity may not be neglected and the treatment of the waste resin becomes extremely difficult. In the measurement of the conductivity of the mixture of the boric acid sample water and the mannitol solution, but in the absence of ion exchange resin in order to avoid the disadvantage as hereinbefore described, it has been found that the resulting determinations of the boron concentration varies in relation to the Li-ion content in the sample water.

In view of the foregoing fact, it has been found that the ideal automatic determination of boron and Li-ion concentrations may be carried out without any conventional disadvantage when the first and the second electrodes for measuring conductivity are arranged, respectively, before and following the mixing of the boric acid sample water with the mannitol solution. The Li-ion concentration is determined by measuring the conductivity of the sample water before the mixing with the mannitol. The boron concentration including errors is determined by measuring the conductivity of the sample water after the mixing with the mannitol. The two measurements thus obtained are put into the calculating circuit to carry out the calculation for correction depending on the variation of the conductivity in the presence of Li-ion, and the resulting determinations are indicated by an indicator.

Thus, after the measurement $k_1$ ($\mu\upsilon$/cm) with the first electrode before the mixing of the sample water with the mannitol solution and the measurement $k_2$ ($\mu\upsilon$/cm) with the second electrode after the mixing has been effected, the boron concentration $C_B$ (p.p.m.) may be calculated using the known equation with the afore-mentioned $k_2$. For example, when the mixing ratio of the sample water with the mannitol solution (10 W/O) is 1:1, the equation is as follows:

$$\sqrt{C_B} = \{6.25 \times 10^{-2}(\log k_2 - 1.95)^2 + 0.1968\} k_2 \quad (1)$$

The boron concentration $C_B$ thus obtained, however, includes an error due to the Li-ion content because the conductivity has been measured in the presence of the Li-ion. Therefore, the boron concentration $C_B$ (p.p.m.) should be corrected to eliminate the effect of the Li-ion concentration $C_{Li}$ (p.p.m.).

Accordingly, the relationship between the Li-ion concentration $C_{Li}$ (p.p.m.) and the measurement of the conductivity $k_i$ ($\mu\upsilon$/cm) is determined with the parameter of the boron concentration $C_B$ (p.p.m.) to obtain the characteristic lines as shown in FIG. 1. From the characteristic lines the Li-ion concentrations $C_{Li}$ (p.p.m.) may be calculated on the basis of the measurement $k_1$ ($\mu\upsilon$/cm), according to the following three equations:

(1) In case of the boron concentration $C_B$ being 1,500 to 3,000 p.p.m.

$$C_{Li}(\text{p.p.m.}) = 0.099 k_1 - 0.43 \quad (2)$$

(2) In case of the boron concentration $C_B$ being 500 1 to 1,500 p.p.m.

$$C_{Li}(\text{p.p.m.}) = 0.093 k_1 - 0.28 \quad (3)$$

(3) In case of the boron concentration $C_B$ being 250 to 500 p.p.m.

$$C_{Li}(\text{p.p.m.}) = 0.093 k_1 - 0.21 \quad (4)$$

Thus, the Li-ion concentration may be obtained.

On the other hand, the relationship between the Li-ion concentration $C_{Li}$ (p.p.m.) and the measurement $k_2$ ($\mu\upsilon$/cm) is determined with the parameter of the boron concentration $C_B$ (p.p.m.) to obtain the characteristic lines as shown in FIG. 2. From these characteristic lines, the boron concentration $C_B$ (p.p.m.) may be correctly calculated on the basis of Li-ion concentration $C_{Li}$ (p.p.m.) and the measurement $k_2$ ($\mu\upsilon$/cm) according to the following equations:

(1) In case of the boron concentration $C_B$ being 500 to 3000 p.p.m. before correction;

$$\sqrt{C_B} = [[6.25 \times 10^{-2} [\log \{k_2 + 4.22 \, C_{Li}(\log k_2 - 0.072)\} - 1.95]^2 + 0.1968]] \cdot \{k_2 + 4.22 \, C_{Li}(\log k_2 - 0.072)\} \quad (5)$$

(2) In case of the boron concentration $C_B$ being 250 to 500 p.p.m. before correction;

$$\sqrt{C_B} = [[6.25 \times 10^{-2} [\log \{k_2 + 4.07 \, C_{Li}(\log k_2 - 0.234)\} - 1.95]^2 + 0.1968]] \cdot \{K_2 + 4.07 \, C_{Li}(\log k_2 - 0.234)\} \quad (6)$$

Moreover, we have devised a new apparatus for determination of the boron concentration through measurement of the conductivity of the mixture of the boric acid sample water with the mannitol solution. In this apparatus, a heat sensitive element of metallic filament, which is sharply sensitive to a liquid temperature at a conductivity measuring position, is dipped in a conductivity measuring tank to detect the change of the liquid temperature by means of variation of an electric resistance; this enables correction of errors in measurements of the conductivities on account of changes of the temperature. The conductivity of the sample water consisting of the boric acid-mannitol complex has a negative temperature coefficient of 0.36% per 1° C. in the range of temperature of from 20° C. to 40° C., so that use of a metallic filament having a positive temperature coefficient, which is connected to a temperature correction circuit of the conductivity measuring circuit results in the convenient measurement of the conductivity with the corrected temperatures.

OBJECTS OF THE INVENTION

Accordingly, a general object of the invention is to provide an apparatus including a calculating circuit for automatic determination of the boron concentration with the Li-ion concentration, in which the conductivity of the sample of the primary cooling water is measured before and after the sample water is mixed with a mannitol solution; the Li-ion concentration is calculated from the measurement obtained; and the correct boron concentration is calculated with correction based on the Li-ion concentration.

A principal object of the invention is to provide an automatic apparatus having an automatic Li-ion correction circuit for continuous determination of boron and Li-ion concentrations through determination of conductivity of a mixture of a boric acid sample water with a mannitol solution, characterized in that a first electrode and a second electrode for measurement of conductivity are arranged, respectively, before and following a mixer for mixing the sample water with the mannitol solution and a calculating circuit using the measurements with the electrodes is provided for calculation of the Li-ion concentration as well as calculation of the correct boron concentration in relation to the Li-ion content.

Another object of the invention is to provide an automatic apparatus in which the calculating circuit calculates the Li-ion concentration $C_{Li}$ (p.p.m.) from the conductivity measurement $k_2$ ($\mu\upsilon$/cm) with the second electrode and $k_1$ ($\mu\upsilon$/cm) with the first one; automatically selects either one of the following equation (5) or (6) based on the boron concentration $C_B$ (p.p.m.) calculated from the conductivity measurement $k_2$ ($\mu\upsilon$/cm) obtained with the second electrode:

(1) in case of the $C_B$ being 500 to 3,000 p.p.m.

$$\sqrt{C_B} = [[6.25 \times 10^{-2} [\log \{k_2 + 4.22 \, C_{Li}(\log k_2 - 0.072)\} - 1.95]^2 + 0.1968]] \cdot \{k_2 + 4.22 \, C_{Li} (\log k_2 - 0.072)\} \quad (5)$$

(2) in case of the $C_B$ being 250 to 500 p.p.m.

$$\sqrt{C_B} = [[6.25 \times 10^{-2} [\log \{k_2 + 4.07 \, C_{Li}(\log k_2 - 0.234)\} - 1.95]^2 + 0.1968]] \cdot \{k_2 + 4.07 \, C_{Li}(\log k_2 - 0.234)\} \quad (6);$$

said calculating circuit introduces the calculated Li-ion concentration $C_{Li}$ (p.p.m.) into either one of said equations (5) or (6); calculates the corrected boron concentration $C_B$ (p.p.m.); and indicates and/or records the calculated result.

Further, another aspect of the invention is to provide the automatic apparatus in accordance with the invention, in which provision is made of a heat sensitive element to determine changes of the temperatures of the passing mixture of the boric acid sample water with the mannitol solution, said heat sensitive element being associated in a measuring circuit of an electric conductivity measuring unit for correction of errors in the measurement of the conductivity on account of changes of the temperatures of the passing mixture.

Other objects and advantages of the invention will be apparent from the following description in connection with the accompanying drawings.

BRIEF DESCRIPTION OF THE DRAWINGS

FIG. 1 shows the characteristic lines representing the relationship between the conductivity $k_1$ ($\mu$ ʊ/cm) and the Li-ion concentration $C_{Li}$ (p.p.m.) contained in the sample water, wherein the conductivity $k_1$ is a value determined before the sample water is mixed with the mannitol solution;

FIG. 2 shows the characteristic lines representing the relationship between the conductivity $k_2$ ($\mu$ ʊ/cm) and the Li-ion concentration $C_{Li}$ (p.p.m.) in the sample water wherein the conductivity $k_2$ is a value determined after the sample water has been mixed with the mannitol solution;

DESCRIPTION OF THE INVENTION AND THE PREFERRED EMBODIMENTS

Figure 3:
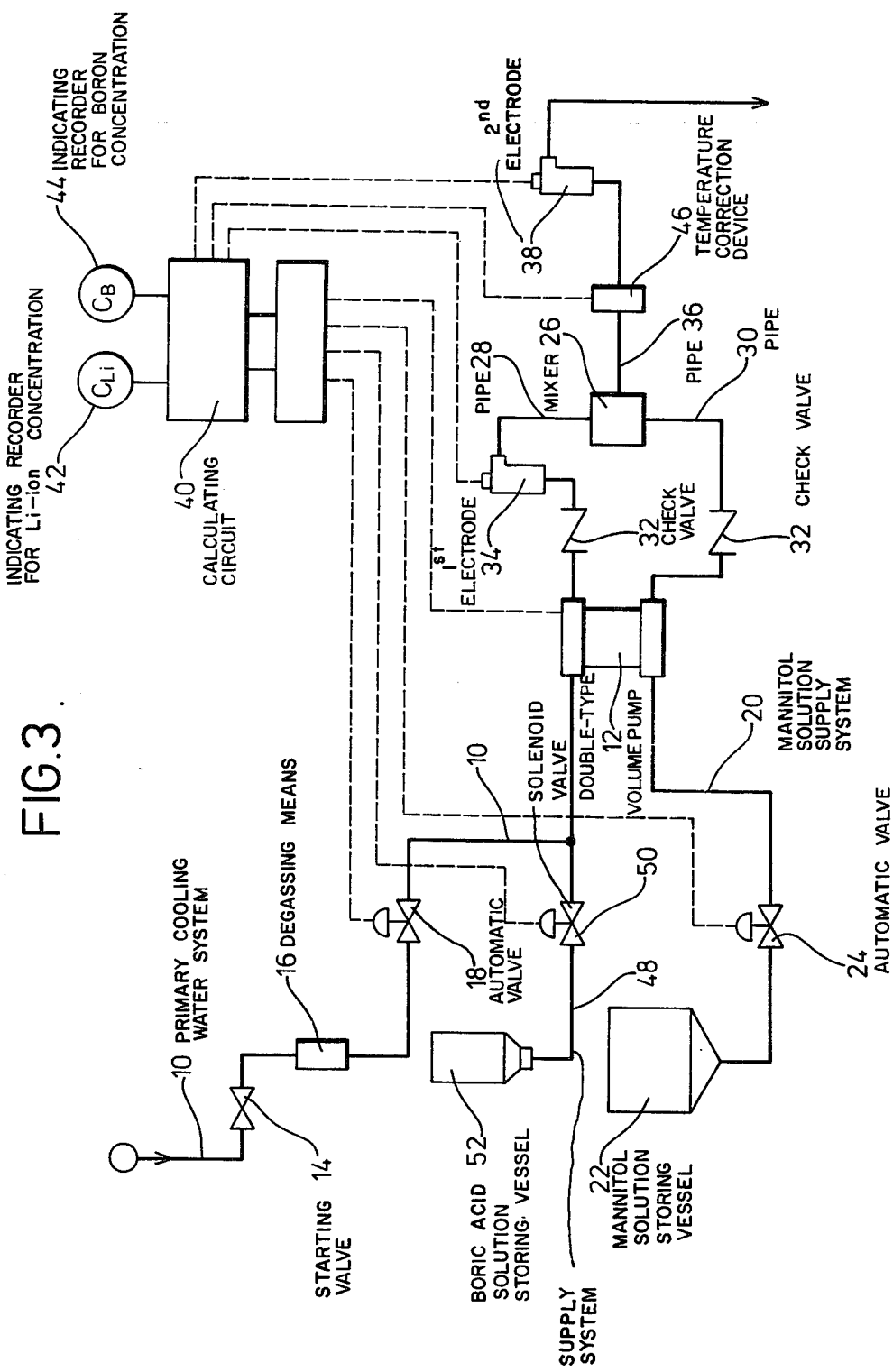
FIG. 3 is the system diagram showing the automatic determination apparatus for the boron and the Li-ion concentrations in accordance with the invention.

In FIG. 3, the reference numeral 10 denotes the primary cooling water system of the pressurized water reactor in which the primary cooling water is supplied to one chamber of a double-type volume pump 12 through a starting valve 14, a degassing means 16 and an automatic valve 18. The reference numeral 20 denotes the mannitol solution supplying system derived from a storing vessel 22 for the mannitol solution, whereby the mannitol solution is supplied to the other chamber of the double-type volume pump 12 through an automatic valve 24.

Then, the primary cooling water and the mannitol solution transferred by the pump 12 are supplied to a mixer 26 through pipes 28, 30 having check valves 32, 32 respectively.

The pipe 28 for the primary cooling water is provided with the first electrode 34 for the conductivity measurement by which the conductivity of the primary cooling water is measured before the mixing with the mannitol solution.

The primary cooling water and the mannitol solution are mixed at a predetermined ratio in the mixer 26, and then the mixture is led to a drain through a pipe 36. The pipe 36 is provided with the second electrode 38 by which the conductivity of the mixed primary cooling water-mannitol solution is measured. The calculating circuit 40 is constituted in such manner that the boron concentration $C_B$ (p.p.m.) after mixing of the sample water with the mannitol solution in the ratio of 1:1, is calculated according to the measurement $k_2$, made with the electrode 38, as follows:

$$\sqrt{C_B} = \{6.25 \times 10^{-2} (\log k_2 - 1.95)^2 + 0.1968\} \, k_2 \quad (1)$$

Then, the calculating circuit 40 selects either one of the three under-mentioned calculating equations (2) to (4) depending on the boron concentration $C_B$ (p.p.m.), calculated according to the equation (1), to calculate the Li-ion concentration $C_{Li}$ (p.p.m.), thereby to correct the error in the boron concentration $C_B$ (p.p.m.) calculated according to the equation (1).

(1) In case of the $C_B$ being 1500 to 3000 p.p.m.

$$C_{Li}(\text{p.p.m.}) = 0.099 \, k_1 - 0.43 \quad (2)$$

(2) In case of the $C_B$ being 500 to 1,500 p.p.m.

$$C_{Li}(\text{p.p.m.}) = 0.093 \, k_1 - 0.28 \quad (3)$$

(3) In case of the $C_B$ being 250 to 500 p.p.m.

$$C_{Li}(\text{p.p.m.}) = 0.093 \, k_1 - 0.21 \quad (4)$$

Preferably, the Li-ion concentration $C_{Li}$ (p.p.m) may be indicated visually or recorded by means of an indicator or a recorder.

Further, the calculating circuit 40 is additionally constituted so as to correct the error of the boron concentration $C_B$ (p.p.m.), calculated using the equation (1), on the basis of the Li-ion concentration $C_{Li}$ (p.p.m.) calculated using the equations (2) to (4) and the conductivity measurement $k_2$ ($\mu$ ʊ/cm) obtained from the second measuring electrode 38. In this case, the circuit is also constituted so as to automatically select either one of the following equations (5) or (6), depending on the boron concentration calculated according to the equation (1).

(1) In case of the $C_B$ being 500 to 3,000 p.p.m.;

$$\sqrt{C_B} = [[6.25 \times 10^{-2} [\log \{k_2 + 4.22 \, C_{Li}(\log k_2 - 0.072)\} - 1.95]^2 + 0.1968]] \cdot \{k_2 + 4.22 \, C_{Li}(\log k_2 - 0.072)\} \quad (5)$$

(2) In case of the $C_B$ being 250 to 500 p.p.m.;

$$\sqrt{C_B} = [[6.25 \times 10^{-2} [\log \{k_2 + 4.07 \, C_{Li}(\log k_2 - 0.234)\} - 1.95]^2 + 0.1968]] \cdot \{k_2 + 4.07 \, C_{Li}(\log k_2 - 0.234)\} \quad (6)$$

Preferably, the boron concentration $C_B$ (p.p.m.) thus calculated may be indicated visually or recorded by means of an indicator or a recorder.

Figure 4:
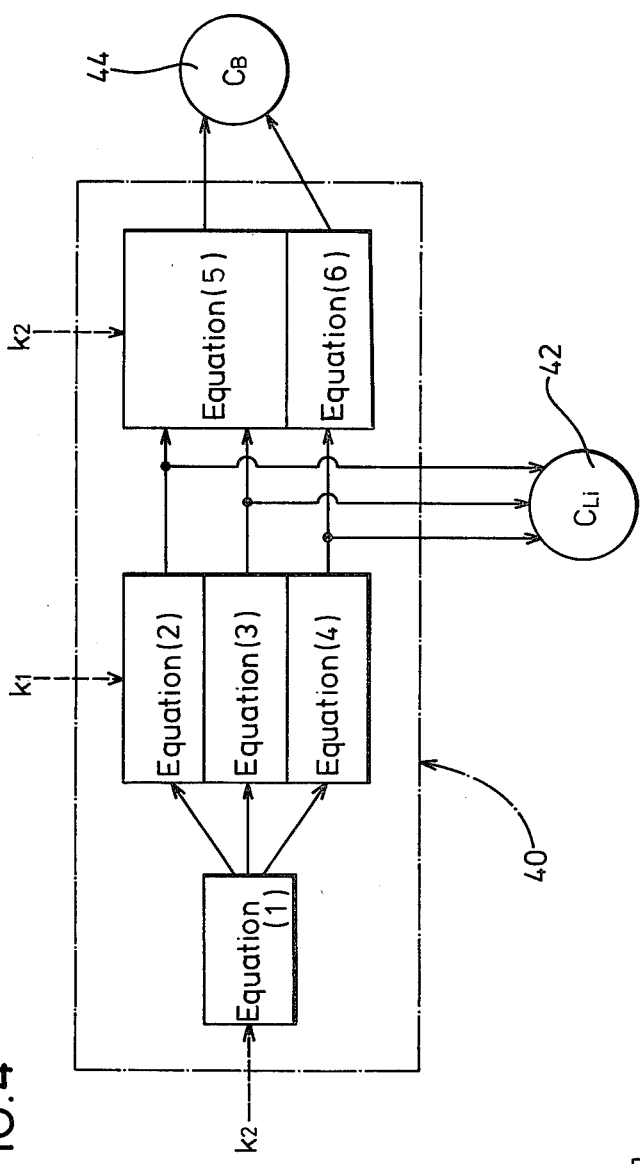
FIG. 4 is the system diagram for the calculation circuit using the determinations made by the apparatus of FIG. 3.

Hereinafter, the Example of determination of the boron and Li-ion concentrations (calculating operation)

in accordance with the invention will be illustrated with reference to FIG. 4.

1. The conductivity $k_1$ ($\mu\upsilon$/cm) of the primary cooling water is measured with the first measuring electrode 34 before mixing with the mannitol solution, and the measurement is transmitted to the calculating circuit 40 and registered.

2. The conductivity $k_2$ ($\mu\upsilon$/cm) of the primary cooling water-mannitol solution mixture is measured with the second measuring electrode 38, and the measurement is transmitted to the calculating circuit 40 and registered.

3. The boron concentration $C_B$ (p.p.m.) including the error is calculated according to the equation (1) on the basis of the conductivity $k_2$.

4. One of the equations (2)-(4) for the Li-ion concentration $C_{Li}$ (p.p.m.) is automatically selected depending on the calculation result of the above boron concentration $C_B$, and the Li-ion concentration $C_{Li}$ (p.p.m.) is calculated from the measurement of the conductivity $k_1$ according to the selected one of the equations.

5. The calculation result of the Li-ion concentration $C_{Li}$ is indicated by the indicating recorder 42.

6. Either one of the correcting equations (5) or (6) for the boron concentration $C_B$ is automatically selected depending on the calculation result of the above boron concentration $C_B$; and the correcting calculation for the boron concentration $C_B$ is effected from the Li-ion concentration and the conductivity $k_2$ according to the selected one of the equations.

7. The calculation result of the boron concentration $C_B$ is indicated by the indicating recorder 44.

Figure 5:
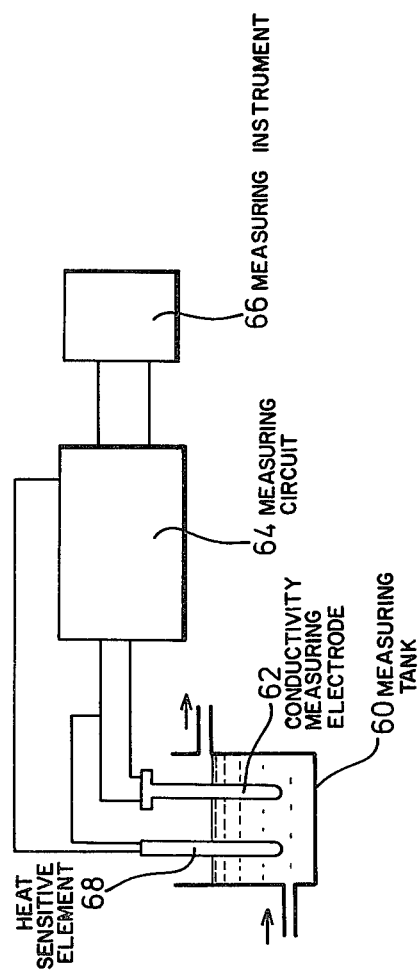
FIG. 5 shows a temperature correction device used in the apparatus in accordance with the invention.

In the apparatus of the invention, it is preferred to arrange the temperature correction device 46 on the pipe 36 for the mixture of the primary cooling water with the mannitol solution and to correct the error from the temperature change of the mixture. As shown in FIG. 5, the measuring tank 60 receives a conductivity measuring electrode 62 which is connected through a lead wire to a measuring circuit 64 including an amplifier (not shown) for measurement of the conductivity in proportion to the boron concentration of the mixture. The conductivity thus measured in the measuring circuit 64 is indexed by a measuring instrument 66 connected to an output of the measuring circuit 64 in the forms of the conductivity or the boron concentration.

In this embodiment of the apparatus according to the invention, a heat sensitive element 68 having a positive temperature coefficient is made of, for example, copper wire, platinum wire, nickel wire or the like and shaped into a coil for reception by a protective sleeve of relatively thin thickness so as to provide a sharp heat sensitive property. The heat sensitive element 68 with the protective sleeve is positioned in the measuring tank 60 to detect the change of the temperature as revealed by the change of resistance. In the example, the heat element 68 is connected to the conductivity measuring circuit 64 (connected to the conductivity measuring electrode 62), thereby to provide a correction circuit which permits an automatic measurement of the conductivity of the mixed cooling water-mannitol solution.

Returning to FIG. 3, the supply system 48 of the boric acid solution for calibration is conveniently connected with the primary cooling water system 10 communicating to the one chamber of the double-type volume pump 12, and is connected with the storing vessel 52 of the boric acid solution via a solenoid valve 50 so as to optionally calibrate the operation of the calculating circuit 40. For the latter purpose, the primary cooling water system 10 is, of course, blocked by means of the valve 18.

According to the apparatus of this invention, the conductivities are measured before and after the boric acid sample water is mixed with the mannitol solution, thereby making it possible to determine the boron concentration properly and rapidly, such concentration having been corrected automatically for the error based on the Li-ion content. Further, the Li-ion concentration in the boric acid sample water may also be determined automatically, facilitating the maintenance and the control of the pressurized water reactor.

While certain preferred embodiments of the invention have been illustrated by way of example it will be understood that any known circuit structure may optionally be employed for the calculating circuit according to the invention and that various modifications may be made without departing from the scope of the invention.

What is claimed is:

1. An automatic apparatus for continuous determination of boron and lithium-ion concentrations in the primary cooling water used in a pressurized water reactor plant comprising, means for conducting a source of boric acid sample water containing lithium ions to a mixer, means for conducting a mannitol solution to said mixer thereby to form in said mixer a boric acid-mannitol complex sample water, a first electrode contacting said boric acid sample water to measure the conductivity thereof, a second electrode contacting the boric acid-mannitol complex sample water as it leaves the mixer to measure the conductivity thereof, a calculating circuit connected with each of the said electrodes for receiving the conductivity measurements emanating therefrom, said calculating circuit including elements for calculating the boron and lithium-ion concentrations of the sample water by utilization of the conductivity measurements, and at least one indicating recorder connected to said calculating circuit for indicating and recording the boron and lithium-ion concentrations.

2. Apparatus according to claim 1, wherein an electrical temperature correction device is located between the mixer and the second electrode for continuously determining the temperature of the boric acid-mannitol complex sample water, said temperature correction device being electrically connected to said calculating circuit to feed electrical impulses thereto, said impulses serving to correct the calculated boron and lithium-ion concentrations.

3. Apparatus according to claim 2, wherein the temperature correction device comprises a measuring tank having an inlet and an outlet, for receiving the boric acid-mannitol complex sample water, a heat sensitive element and a conductivity measuring electrode, each contacting the sample water in said measuring tank, a measuring circuit connected electrically to the heat sensitive element and to the conductivity measuring electrode, and a measuring instrument connected electrically to the measuring circuit.

4. Apparatus according to claim 3, wherein the heat sensitive element has a positive temperature coefficient and is made of copper, platinum, or nickel wire.

5. Apparatus according to claim 4, wherein the heat sensitive element is located inside a thin walled protective sleeve.

6. Apparatus according to claim 1, wherein the calculating circuit comprises a first element for calculating the boron concentration $C_B$ of the sample water containing the Li-ion by use of the conductivity measurement $k_2$ of the second electrode according to the equation (1):

$$\sqrt{C_B} = \{6.25 \times 10^{-2}(\log k_2 - 1.95)^2 + 0.1968\} k_2 \qquad (1);$$

a second element for automatically selecting one of the following equations (2) to (4) depending on the calculated value of $C_B$:

(a) in case of $C_B$ being 1,500 to 3,000 p.p.m.

$$C_{Li} = 0.099 k_1 - 0.43 \qquad (2)$$

(b) in case of $C_B$ being 500 to 1,500 p.p.m.

$$C_{Li} = 0.093 k_1 - 0.28 \qquad (3)$$

(c) in case of $C_B$ being 250 to 500 p.p.m.

$$C_{Li} = 0.093 k_1 - 0.21 \qquad (4)$$

a third element for introducing the conductivity measurement $k_1$ of the first electrode into the selected equation (2) to (4);

a fourth element for calculating the accurate Li-ion concentration $C_{Li}$;

a fifth element for automatically selecting one of the following equations (5) or (6) depending on the boron concentration $C_B$ calculated by the first element:

(d) in case of the $C_B$ being 500 to 3,000 p.p.m.

$$\sqrt{C_B} = [[6.25 \times 10^{-2} [\log \{k_2 + 4.22 C_{Li}(\log k_2 - 0.072)\} - 1.95]^2 + 0.1968]] \cdot \{k_2 + 4.22 C_{Li}(\log k_2 - 0.072)\} \qquad (5)$$

(e) in case of the $C_B$ being 250 to 500 p.p.m.

$$\sqrt{C_B} = [[6.25 \times 10^{-2} [\log \{k_2 + 4.07 C_{Li}(\log k_2 - 0.234)\} - 1.95]^2 + 0.1968]] \cdot \{k_2 + 4.07 C_{Li}(\log k_2 - 0.234)\} \qquad (6);$$

a sixth element for introducing the Li-ion concentration $C_{Li}$ calculated by the fourth element into the selected equation (5) or (6); and a seventh element for calculating the accurate boron concentration.

* * * * *